United States Patent [19]

Wertheimer et al.

[11] Patent Number: 4,535,316

[45] Date of Patent: Aug. 13, 1985

[54] HEATED TITANIA OXYGEN SENSOR

[75] Inventors: Harry P. Wertheimer, Findlay, Ohio; Thomas A. Libsch, Novi, Mich.; Jerome L. Pfeifer, Livonia, Mich.; Paul C. Becker, Bloomfield Hills, Mich.

[73] Assignee: Allied Corporation, Morristown, N.J.

[21] Appl. No.: 593,076

[22] Filed: Mar. 26, 1984

[51] Int. Cl.³ .................. G01N 27/46; G01N 27/12; H01L 7/00

[52] U.S. Cl. .......................... 338/34; 73/23; 73/27 R; 422/94; 422/98

[58] Field of Search ............. 338/34; 73/23, 27 R; 422/94, 98

[56] References Cited

U.S. PATENT DOCUMENTS

| 3,886,785 | 6/1975 | Stadler et al. | 73/27 R X |
| 3,915,135 | 10/1975 | Kushida et al. | 338/34 X |
| 4,007,435 | 2/1977 | Tien | 338/34 |
| 4,147,513 | 4/1979 | Bienkowski et al. | 338/34 X |
| 4,377,944 | 3/1983 | Hishii et al. | 338/34 |
| 4,453,397 | 6/1984 | Ohta et al. | 338/34 X |

FOREIGN PATENT DOCUMENTS

| 2608487 | 9/1976 | Fed. Rep. of Germany | 422/98 |
| 58-24850 | 2/1983 | Japan | 73/23 |
| 58-124943 | 7/1983 | Japan | 73/23 |

OTHER PUBLICATIONS

Logothetis et al., "TiO₂ Film Oxygen Sensors Made by CVD from Organometallics", Sensors and Actuators, vol. 4, (1983), pp. 333-340.

Primary Examiner—Roy N. Envall, Jr.
Assistant Examiner—C. N. Sears
Attorney, Agent, or Firm—Leo H. McCormick, Jr.; Ken C. Decker

[57] ABSTRACT

A heated resistive type sensor (20) for detecting the oxygen content in an exhaust gas is connected to an electronic control unit (22) for regulating the air/fuel ratio used to operate an internal combustion engine (10). The sensor (20) has a heater (70) which provides a constant thermal energy level to a titania sensing element (76) whose resistance to the flow of electrical current is directly related to the percentage of oxygen in the exhaust gas. The electrical resistance is used as a control signal to maintain the air/fuel ratio within set limits. The resistive portion consists of three resistive elements, one that senses $O_2$ that is made of titania - $TiO_2$, the other two resistors are thick film type connected in series thereto. Finally, the gas sensing layer and electrode leads attached thereto are covered by a protective glass layering to prevent contamination of the sensor element.

5 Claims, 4 Drawing Figures

HEATED TITANIA OXYGEN SENSOR

This invention relates to a resistive type sensor for detecting oxygen in an exhaust gas through which an air to fuel ratio is maintained to operate an engine. The sensor has a substrate with a thick film resistive heater on one side and a titania film on the other side. The resistance of the titania film to the flow of electrical current (which is related to the percentage of oxygen in the exhaust gas) forms an operation signal to provide a control unit with an input. The control unit regulates the fuel supplied to the engine.

Three-way catalytic converters used on automotive engines are the most commonly used method for meeting the emissions requirements established by the regulations set forth in the Clean Air Act of Dec. 31, 1970 in the United States. When a closed loop system having a catalytic converter is used, an oxygen sensor is located in the exhaust manifold to provide a feedback signal to an electronic control unit. The electronic control unit maintains the engine input air to fuel ratio as near stoichiometry as possible for peak catalytic converter efficiency by measuring the oxygen content in the exhaust gas. Both galvanic (zirconia) and resistive (titania) oxygen sensors have been evaluated as a way to measure the oxygen content in an exhaust gas.

In galvanic sensors, zirconium dioxide electrolytic material develops a potential in accordance to the following Nernst equation:

$$E = \frac{RT}{4F} \ln[PO_2(\text{side 1})/PO_2(\text{side 2})]$$

where R is the universal gas constant, T the temperature in degrees Kelvin, F the Farady constant, and $PO_2$ the partial pressure of oxygen. The voltage potential (E) results from a difference in the partial pressure of oxygen between the two sides of the electrolyte where side 1 is normally exposed to an atmospheric gas reference and side 2 is exposed to the exhaust gas. Generally, exhaust temperatures above 350° C. are required for such sensors to function.

For oxygen sensor applications of the type disclosed in U.S. Pat. Nos. 3,835,012 and 4,107,018, the zirconia ceramic is shaped into a non-porous thimble where the inside remains exposed to atmospheric air for establishing the reference oxygen partial pressure while the outside or exterior is exposed directly to the exhaust gas. With a porous noble metal catalytic film applied to the exterior and interior surfaces of the thimble, the equilibrium partial pressure of oxygen in the exhaust gas can then be compared to the atmospheric reference.

Over the typical 350° C. to 800° C. exhaust gas operating conditions, a zirconia sensor output will be about 50 mV when the exhaust is lean, and about 900 mV when the exhaust is rich. Since the exhaust gas partial pressure of the oxygen term in the Nernst equation is a function of temperature, then when the $PO_2$ term is combined with the direct dependent term, T, the actual voltage output, E, becomes somewhat independent of temperature, at least in consideration for stoichiometric operation. Further, in order for a zirconia sensor to operate properly, the thimble must be non-porous to maintain a proper atmospheric reference.

In an effort to simplify the sensor it was suggested in U.S. Pat. Nos. 4,007,435; 4,147,513; 4,377,801 and 4,387,359 that titanium dioxide could be substituted for zirconia.

Titanium dioxide is a semiconductor material which has defects in the crystal lattice whose number is dependent on temperature, T, and the partial pressure of oxygen, $PO_2$, in the gas environment surrounding the semiconductor. Under lean exhaust conditions the lattice remains nearly complete while under rich conditions there is a large number of oxygen vacancies and titania ion interstitials. These lattice defects within the semiconductor, are donors which free electrons into the conduction band, thus decreasing the resistance. The resistance of the semiconductor, $R_T$, can be measured by the following equation:

$$R_T \alpha [PO_2(\text{exhaust})]^n \exp(E/KT)$$

where E is the activation energy, and K is Boltzmann's constant, and n is approximately equal to $\frac{1}{4}$ over the temperature range of interest. As seen by this proportionality, there is no dependency upon a reference partial pressure of oxygen. A resistance change of between 3 to 5 orders of magnitude is typical when switching between rich and lean operation within the 350° to 800° C. temperature range.

In operation, when a titania element, $R_T$, is put into a voltage divider circuit with $R_c$ and a compensating resistor, inserted between the $TiO_2$ element and ground, the output voltage, $V_o$, as measured across $R_c$ is given by the following equation:

$$V_o = [R_c/(R_T + R_c)]V_{in}$$

where $V_{in}$ is the input voltage. The compensating resistor $R_c$, ideally is selected to be midway on a logarithmic scale between the rich and lean resistance values of the titania element ($R_c = [R_T(\text{Rich})R_T(\text{Lean})]^{\frac{1}{2}}$). This permits the output signal to go from near zero on lean exhaust to near full value (of the input voltage) on rich exhaust, thus simulating the switching characteristics of a $ZrO_2$ sensor.

While there is some flexibility in selecting the value for $R_c$, good sensor switching can be maintained if the selected resistance remains at least an order of magnitude above the rich and below the lean limits of the $TiO_2$ element. However, it is impossible to find one fixed resistor value which maintains sensor function completely over the typical 350° C. to 800° C. operating temperature range of the exhaust gas due to variation in resistance of the $TiO_2$ element with temperature.

Temperature dependency of a titania sensing element can be compensated by having a variable resistor which would track the changing resistance of the titania film or by maintaining the titania element at a fixed temperature which would permit the use of a fixed value resistor.

When a variable resistor is used, the variable resistor is a negative temperature coefficient thermistor which matches the temperature resistance variation of the titania sensing element and is located in the exhaust gas. A cost effective NTC thermistor which remains stable and durable in an exhaust gas environment has yet to be demonstrated.

In order to use a fixed value resistor, it is necessary to heat the titania sensing element to the highest temperature expected to be produced by the exhaust gas. Since the fixed resistor does not need to be located in the exhaust gas stream, a low cost thick film resistor that is commercially available may be used.

According to the principals of this invention a resistive type sensor was constructed as follows:

A band of an electrically conductive material (i.e. platinum) was printed on a first side of a flat alumina substrate as a thick film. This band formed a loop that extended from a first end to adjacent a second end where the width was reduced to establish a pattern. One lead from the loop is connected to a voltage source and the other end is connected to an electrical ground. The resistance to the flow of electrical current through the band generates thermal energy. The pattern is of such a design that substantially most of the thermal energy is generated at the second end of the substrate. The electrical resistance of the platinum thick film, which increases with temperature, reduces power generated at the second end of the substrate as the temperature of the exhaust gas increases, thus keeping the substrate temperature at a substantially fixed level.

The second side of the substrate contains a metal electrode, a titania sensing film, and two fixed value resistors.

A conductive metal having high temperature durability such as platinum is applied to the second side of the substrate to form the electrode which consists of three strips.

A first conductive metal strip traverses the length of the substrate from the first end of the substrate to the second end of the substrate. A first fixed resistor is located in this first strip near the first end of the substrate. A first end of the first strip is adapted to be connected to the voltage source.

A second conductive metal strip traverses the length of the substrate from the first end of the substrate to the second end of the substrate substantially parallel to the first strip but not touching the first strip. A first end of the second strip is adapted to be connected to the engine electronic control unit.

A second resistor is located near the first end of the substrate such that the first end of the second resistor is electrically attached to the second strip. The second end of the second resistor is attached to the second end of the third conductive metal strip. A third conductive metal strip traverses from the second resistor to the first end of the substrate. The first end of the third strip is adapted to be connected to an electrical ground.

A titania film applied to the second side of the substrate covers the second ends of the first and second strips. The titania film forms a variable resistive path between the first and second strips. The resistance of the flow of electrical current through the titania film is related to the oxygen content in the exhaust gas and dependent on temperature. However the temperature dependence is substantially negated by the resistance heating of the pattern on the opposite side of the substrate.

The electrical circuit on the second side has one end of the first resistor connected to the (positive) voltage source; the other end of the first resistor is connected to the titania film and the second resistor is connected between the titania film and the ground or negative side of the voltage source. Thus, when the exhaust is rich, the titania resistance is low and the electrical current is relatively high, causing a relatively high voltage drop across said second resistor as measured between said second and third strips. Under lean air to fuel conditions, the titania resistance is relatively high, reducing the voltage drop between the second and third strips.

The voltage drop across second resistor is carried through the second strip as an input signal for operating the electronic control unit which controls the input air to fuel ratio to the engine.

An advantage of this invention occurs through the use of a continuously powered heater such that the temperature of the titania sensing element remains somewhat fixed and thus its resistance to electrical current is a function only of the percentage of oxygen in an exhaust gas. The resistance to the flow of electrical current is communicated to an electronic control unit as an input signal to maintain an air to fuel ratio required to operate an engine within set limits.

It is an object of this invention to provide an oxygen sensor with fixed resistors such that the voltage drop across one of the resistors when the titania sensing element is exposed to varying percentages of oxygen in an exhaust gas is inversely proportional to the resistance of the flow of electrical current through the titania sensor.

It is another object of this invention to provide a sensor which is not limited to operation above some minimum exhaust gas temperature such as 350° C.

A further object of the invention is to provide a sensor which does not require a supply of reference air, and therefore, a sensor which is not affected by outside environmental conditions such as road splash.

A further object of this invention is to provide a sensor element with a protective layering that lessens the chance of unit failure.

Another object of this invention is to provide a sensor which operates directly off the engine battery system and does not need an additional power input lead from the engine electronic control unit.

These objects and advantages should become apparent from reading this specification while viewing the drawing.

Figure 1:
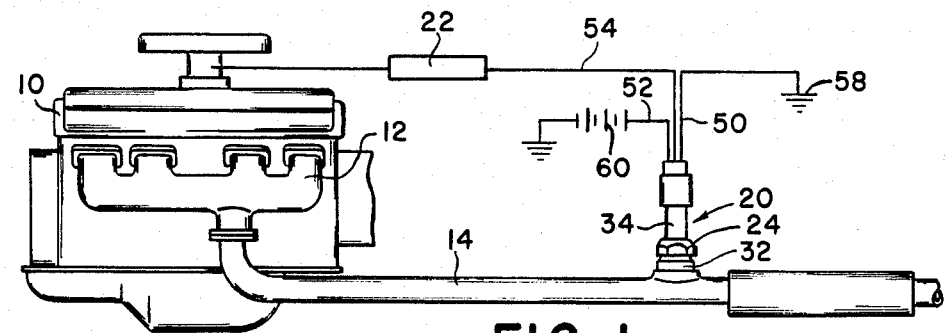
FIG. 1 is a schematic illustration of an exhaust system with an oxygen sensor made according to the principals of this invention located therein.

In FIG. 1 a reciprocating type internal combustion engine 10 is shown with an exhaust manifold 12 connected to a pipe 14 which carries exhaust gas to the surrounding environment.

In carburetor fuel management systems which used a zirconia sensor, the zirconia sensor was located adjacent the exhaust manifold 12 in order to maintain the sensing tip above 350° C. Newer vehicles designed for high fuel efficiency have cooler exhaust, expecially at idle, and may not even generate temperatures above 350° C. during all times when control is required. Further, some exhaust manifold designs necessitate locating the sensor farther from the exhaust ports than was past practice.

The heated titania sensor 20 shown in FIG. 1 which is not dependent on the exhaust gas temperature may be located away from the exhaust manifold 12 at any point in pipe 14. Sensor 20 detects the oxygen content in the exhaust gas and supplies an electronic control unit 22 with an input signal. The electronic control unit 22 reacts to the input signal by controlling the air to fuel ratio supplied to operate engine 10. The correct air to fuel ratio can help to maintain the exhaust gas within the emission standards set by the clean air regulations for the United States.

Figure 2:
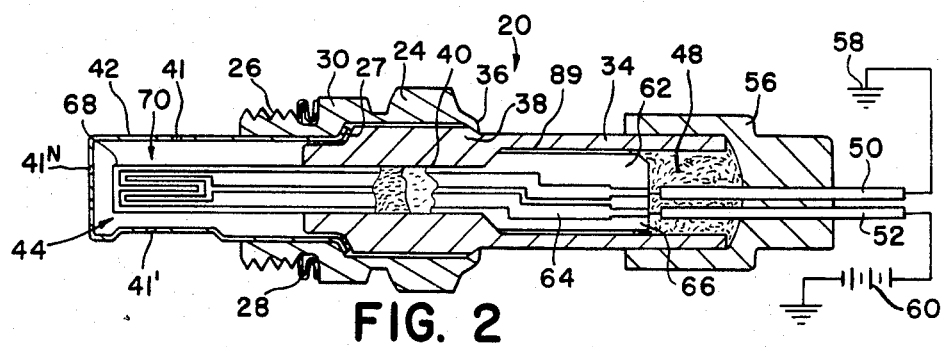
FIG. 2 is a sectional view of a first side of the oxygen sensor of FIG. 1 showing the heater for the sensor.
Figure 3:
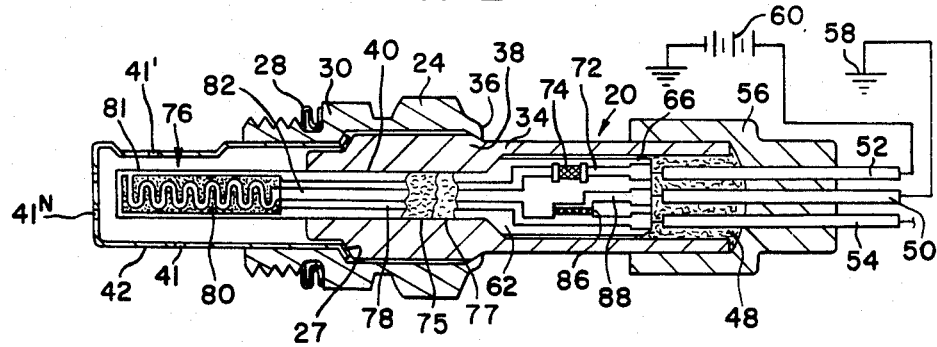
FIG. 3 is a sectional view of a second side of the oxygen sensor of FIG. 1 showing the sensing film and fixed value resistors associated therewith.

The sensor 20 is shown in more detail in FIGS. 2 and 3. The sensor 20 has a metal shell 24 which is attached to pipe 14 and fixture 32 by threads 26. A metal gasket 28 located adjacent head 30 engages fixture 32 to establish a seal between the sensor 20 and pipe 14. The end 36 of shell 24 is crimped around a ledge 38 on insulator 34 to fix the insulator with respect to shell 24. A shield 42 attached to shell 24 protects a sensing element 44 located in slot 40 in the ceramic insulator 34 from damage. A gasket 27 also aids in sealing the insulator 34 and shell 24. Sensing element 44 is held in slot 40 by a cement cap 48 that encases lead 50, 52, and 54 and fills the entire cavity 89 in insulator 34. A boot 56 attached to the ceramic insulator 34 protects the leads 50, 52, and 54 as they exit from the sensor 20. Lead 50 connects resistor 86 and element 44 with an electrical ground 58, lead 52 connects through a resistor 74 the sensing element 44 with a voltage source 60, and lead 54 connects the sensing element 44 and resistor 86 with an electronic control unit 22.

In more particular detail, the sensing element 44 is supported by a flat rectangular insulating substrate (such as alumina) 62. As shown in FIG. 2, a band of electrically conductive material (such as platinum) 64 is applied to one side of the substrate 62 as a thick film. The band forms a continuous loop that extends from the first end 66 to the second end 68 and back to the first end 66. The band has a substantially constant width to a position adjacent the second end 68, where the width is reduced to a pattern 70 which forms a resistance heater at end 68. The electrically conductive material in pattern 70 should have a high positive temperature coefficient of resistance such as the value of $3.8 \times 10^{-3}/°$ C. for platinum.

The electrically conductive material forms a path for the flow of electrical current from voltage source 60 to the electrical ground 58. The resistance to the flow of current increases with temperature and as a result, as the temperature of the exhaust gas increases, the power generated in the pattern area 70 is correspondingly reduced thus maintaining the temperature of the sensing film somewhat fixed. The pattern 70 is selected such that the communication of 14 volts through loop 64 generates a temperature within a band from 650° to 900° C. during engine operation of the sensor 20 in pipe 14.

The sensing side of sensor 20 as illustrated in FIG. 3 has a strip 72 of an electrically conductive thick film (such as platinum of the type disclosed in U.S. Pat. No. 4,469,626), printed on substrate 62. A resistor 74 located in strip 72 adjacent end 66 reduces the voltage supplied to patterned end 76 through lead 52 from source 60. A second strip 78 of an electrically conductive thick film of a noble metal is printed on the second side substantially parallel to the first strip 72. Strip 78 is connected to lead 54. A resistor 86 is connected to strip 78 adjacent end 66. A third strip 88 of an electrically conductive thick film of metal connects resistor 86 to lead 50.

The patterned end 76 is such that strips 72 and 78 never touch each other. A fine particle titania film 80 applied over the pattern 76 forms a variable resistive path between the first and second strips. The titania film 80 is porous and when exposed to exhaust gas has a resistance that changes as the proportion of oxygen in the exhaust gas changes.

Figure 4:
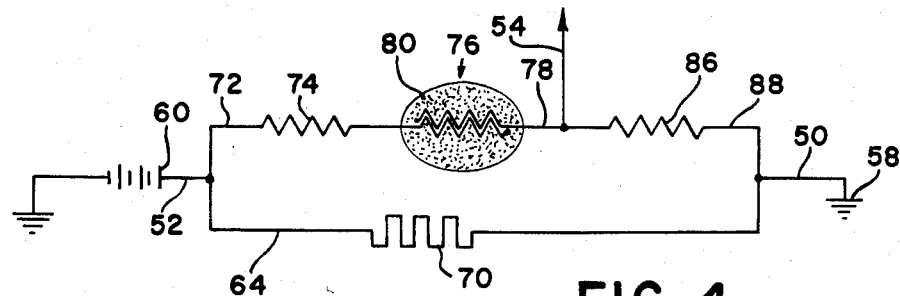
FIG. 4 is a schematic illustration of the electrical circuit for the oxygen sensor of FIG. 1.

The electrical schematic for sensor 20 is illustrated in FIG. 4. The voltage source (60) is typically a 12 volt battery supply; however, taking into consideration the presence of an alternator charging system, the voltage may vary from 11 to 16 volts. Electrical current is carried through lead 52 to loop 64 which causes thermal energy to be generated in the pattern area 70 of the heater side of the sensing element 44. The temperature in the pattern area 70 is maintained between 650° to 900° C. when the sensor is located in the stream of exhaust gas in pipe 14 which has a temperature of from 200° to 850° C.

Resistor 74 is of such a value that the current supplied to end 81 has a value less than 10 milliamps. The current is such that the generation of thermal energy in the titania film 80 is minimal. In addition, resistors 74 and 86 are selected such that the total voltage generated as a signal in the strip 78 varies from 0 to 900 millivolts. The current flow through the thick film 80 approaches zero (0.3 ma) when the content of oxygen in the exhaust gas approaches a lean value (i.e. toward oxygen content of air) with the resulting signal voltage carried through lead 54 to the electronic control unit 22 also approaching zero.

The current flow through the thick film 80 approaches 4-6 ma when the oxygen content in the exhaust gas approaches zero (rich, i.e, $10^{-12}$ to $10^{-18}$ atmospheres). Under rich exhaust conditions and with nominal 14 V power input, the voltage signal supplied to the electronic control unit (22) is about 900 millivolts.

The shield 42 has a sufficient number of openings 41, 41'... $41^N$ that the sampled flow of exhaust gas around 80 is substantially instantaneous. Since the temperature of the pattern area 70 is maintained between 650° and 900° C., the only variable in the sensor operation is the impedence of electrical current flow through the titania film which is related to the oxygen content in the exhaust gas. Thus, this sensor 20 is immediately functional to provide the electronic control unit 22 with an input signal to achieve a desired air to fuel ratio that helps to meet federal clean air requirements.

Under some operating conditions or after an extended period of operating time it is envisioned that carbon present in the exhaust gas could be deposited on the unheated region 82 of the alumina substrate. If sufficient carbon build up occurs an electrical short could develop between strips 78 and 72 and thus provide an improper input signal to the electronic control unit 22. In order to prevent shorting a non-porous dielectric coating 75 such as an alumina silicate glass glaze is applied to cover electrode leads 72 and 78 between titania film 80 and resistors 74 and 86. This same glass glaze 75 is also applied over the heater loop 64 on the substrate 62. This glaze helps to protect the heater element and extend its life when subjected to automotive exhaust gases. These glaze coatings may be applied as a paste using thick film printing techniques which after a high temperature firing forms a non-porous dielectric layer.

In addition, a porous overcoat 77 could then be applied to both sides of the substrate 62 for additional protection of the heater element formed by pattern 60 and of the titania film 80. This porous layer prevents abrasion of the thick films by particles in the exhaust gases and also prevents direct deposition of contamination from the exhaust gases on the titania film surfaces. The overcoat has sufficient porosity to allow the exhaust gas to reach the patterned area 76 for proper sensing performance. One such porous overcoat may be made with alumina particles bound together in a matrix with a borosilicate glass and which may be applied using thick film printing techniques.

Additionally for some applications it may be beneficial to improve the response time of the titania film. This can be accomplished by applying a catalytic agent such as platinum onto the surfaces of the titania particles in the sensing film 80.

While the fixed resistors 74 and 86 are shown as being integrally attached to substrate 62, it is anticipated that these resistors could be remote from the substrate 62 and the resulting operational signal for the electronic control 22 remains the same.

We claim:

1. A resistive type sensor for detecting oxygen in an exhaust gas of an operating engine, said exhaust gas having a temperature of from 200° to 850° C., said sensor supplying an electronic control unit with an input signal to maintain a desired air to fuel ratio for operating said engine, said sensor comprising:

an insulating substrate having a first side and a second side with a first end and a second end;

a band of an electrically conductive thick film located on said first side, said band forming a loop that extends from said first end to said second end, said band having a substantially constant width from said first end to a location adjacent said second end where the band width is reduced, said thick film having an electrical resistance that increases with temperature, said loop having one end connected to a voltage source and its other end connected to an electrical ground, said thick film in resisting the flow of electrical current to said ground creating thermal energy adjacent said second end, said electrically conductive thick film sensor having a positive temperature coefficient of about $3.8 \times 10^{-3}/°$C., said reduced width of said band of electrical conductive thick film having a pattern such that any power loss in the constant width portion of said loop is substantially eliminated to maintain the temperature of said second end within a temperature range of from 650° to 900° C. at substantially all times when voltage is available;

a first strip of an electrically conductive thick film located on said second side and extending from said first end to said second end, said first end of said first strip being connected to said voltage source;

a second strip of an electrically conductive thick film located on said second side and extending from said first end to said second end, said first end of said second strip being connected to said electronic control unit;

a titania film applied to said second ends of said first and second strips to provide an electrical conductive path between said first and second strips;

a third strip of an electrical conductive thick film located on said second side for connecting said second resistor with said electrical ground;

a fixed value resistor connected in series within said first strip;

a second fixed value resistor connected to said second strip and electrical ground, said titania film responding to changes in the amount of oxygen in the exhaust gas by modifying the flow of electrical current in said first strip and said second strip, said first and second fixed value resistors being selected such that the total voltage drop between said second and third strips varies from near 0 to 900 mV as the resistance of said titania film changes from near 100K ohms to near 100 ohms as the amount of oxygen in the exhaust gas correspondingly changes from near $10^{-3}$ to near $10^{-14}$ atmospheres, said resistance to current flow being indicative of said voltage drop and communicated through said second strip as an input signal to operate said control unit;

a coating of alumina borosilicate glass material applied to said titania film to prevent particles in said exhaust gas from being deposited on said electrical conductive path, said glass material having sufficient porosity to allow exhaust gas to flow to said electrical conductive path without effecting the development of said input signal; and a coating of alumina silicate glass glaze applied to said band and to said first and second strips of electrically conductive thick film to prevent carbon particles carried by said exhaust gas from being deposited thereon and establishing electrical conductive shorting paths that could affect the development of said input signal.

2. The resistive sensor as recited in claim 1 wherein said voltage level of said source varies from 11 to 16 volts and said voltage signal that is presented to said electronic control unit varies from 0 to 1030 millivolts.

3. The resistance sensor as recited in claim 1 wherein said first resistor limits the voltage presented to said second end of said first strip under rich exhaust gas conditions to reduce long term degradation of the titania sensing element.

4. The resistance sensor as recited in claim 1 wherein the value and location of said first and second fixed value resistors may be modified to obtain an output signal other than 0 to 900 mV.

5. The resistance sensor as recited in claim 1 further including a catalytic agent applied the titania film to improve the response time of the titania film to changes in the oxygen concentration in the exhaust gas.

* * * * *